United States Patent
Galehr et al.

[11] Patent Number: 6,102,699
[45] Date of Patent: Aug. 15, 2000

[54] SYRINGE FOR DENTAL MATERIAL

[75] Inventors: Klaus Galehr, Schlins, Austria; Peter Kunkel, Triesen, Liechtenstein; Jürgen Mertins, Gams, Switzerland

[73] Assignee: Ivoclar A.G., Schaan, Liechtenstein

[21] Appl. No.: 09/203,298

[22] Filed: Dec. 1, 1998

Related U.S. Application Data
[60] Provisional application No. 60/082,932, Apr. 24, 1998.

[30] Foreign Application Priority Data

Dec. 1, 1997 [DE] Germany .............. 197 53 272

[51] Int. Cl.⁷ .................................................. A61C 5/04
[52] U.S. Cl. .................................................. 433/90; 604/190
[58] Field of Search ...................... 433/89, 90; 604/125, 604/126, 190, 228, 230, 231

[56] References Cited

U.S. PATENT DOCUMENTS

| | | |
|---|---|---|
| 3,512,940 | 5/1970 | Shapiro ................................. 604/231 |
| 3,707,832 | 1/1973 | Muller et al. . |
| 3,751,271 | 8/1973 | Kimura et al. . |
| 3,807,562 | 4/1974 | Goda . |
| 3,938,513 | 2/1976 | Hargest . |
| 3,960,727 | 6/1976 | Hochstrasser . |
| 4,256,470 | 3/1981 | Zajicek et al. . |
| 4,448,206 | 5/1984 | Martell ................................. 604/190 |
| 4,572,210 | 2/1986 | McKinnon ........................... 604/190 |
| 4,732,162 | 3/1988 | Martell ................................. 604/190 |
| 4,957,637 | 9/1990 | Corwell ................................ 604/190 |
| 5,238,003 | 8/1993 | Baidwan et al. .................... 604/190 |

FOREIGN PATENT DOCUMENTS 2593417  7/1987  France .................................... 433/90

*Primary Examiner*—Ralph A. Lewis
*Attorney, Agent, or Firm*—John C. Thompson; Alan S. Korman

[57] ABSTRACT

A syringe for dental material has a cylinder with a dispensing socket and an open end opposite the dispensing socket. A plunger is inserted through the open end into the cylinder and is guided in the cylinder. The plunger is made of a porous, sintered material.

15 Claims, 1 Drawing Sheet

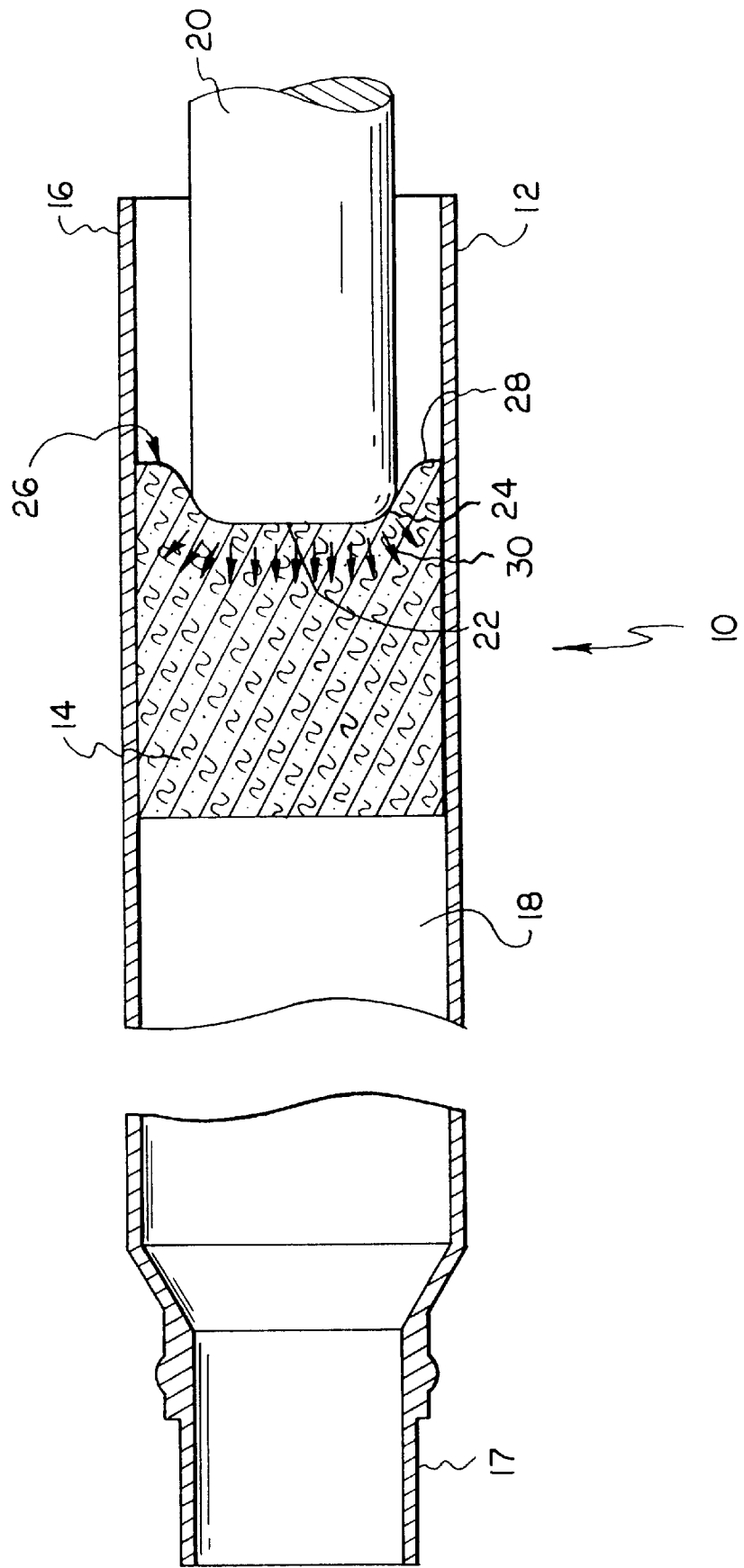

SYRINGE FOR DENTAL MATERIAL

This application claims benefit of Provisional Appl. 60/082,932, filed Apr. 24, 1998.

BACKGROUND OF THE INVENTION

The present invention relates to a syringe, especially for dental materials, comprising a cylinder in which a plunger is guided, whereby the plunger is insertable into the cylinder at an end opposite the dispensing socket of the cylinder.

Such a syringe has already been suggested in U.S. Pat. No. 5,938,439. Such a syringe is especially suitable for dispensing dental materials. Such dental materials may have a relatively great viscosity but may also be rather liquid whereby the manipulation temperature plays an important role.

In order to prevent air inclusion upon pushing the plunger into the cylinder through its open end, which air could be dispensed and reduce the quality of the dental material to a considerable extent, it has been suggested in the past to provide the plunger with a longitudinal bore through which the air could escape. In order to prevent that liquid dental materials could also escape through this longitudinal bore, the dental material is briefly polymerized at the side facing the plunger so that its viscosity is so great that it cannot escape through the longitudinal bore.

This method has been successful especially for light and heat curable dental materials whereby, however, the additional method step of polymerization is required which thus delays the filling process.

Various other methods have been suggested in order to allow for a bubble-free placing of the plunger into the piston while maintaining proper sealing of the syringe and to ensure also safe actuation of the syringe. When a gap is provided around the edge, this can cause canting of the plunger especially when it is relatively short with respect to its diameter. Also, the push rod which is used for actuating the plunger, can easily be soiled by the dental material or may get caught in the cylinder.

It is therefore an object of the present invention to provide a syringe of the aforementioned kind, which while maintaining operational safety, prevents reliably the presence of air inclusions when placing the plunger into the cylinder, whereby, however, the manufacturing costs should be reduced also.

SUMMARY OF THE INVENTION

The syringe for dental material according to the present invention is primarily characterized by:
  a cylinder having a dispensing socket and an open end opposite the dispensing sockets;
  a plunger inserted through the open end into the cylinder and guided in the cylinder;
  the plunger comprised of a porous, sintered material.

Preferably, the porous, sintered material has pores of a pore diameter of 2 to 8 micrometer measured according to DIN 30911 and/or ISO 4003.

Preferably, the pore diameter is 5 micrometer.

Advantageously, the pore size of the porous, sintered material is 50 to 120 micrometer measured according to DIN 30911 and/or ISO 4003.

Preferably, the, pore size is 70 micrometer.

Advantageously, the porous, sintered material has a porosity of 30% to 60%.

The porous, sintered material has micropores.

Advantageously, the porous, sintered material is comprised of polyethylene.

The polyethylene contains preferably a binder for increasing stability.

The porous, sintered material is advantageously comprised of a hydrophobic plastic material.

The porous, sintered material may be comprised of thermoplastic material.

The porous, sintered material has preferably a density of 0.4 to 0.8 $g/cm^3$, preferably a density of 0.6 $g/cm^3$.

The porous, sintered material is advantageously comprised of a ceramic material.

The syringe preferably further comprises a push rod acting on the end of the plunger facing away from the dispensing socket for elastically deforming the plunger. The push rod has a diameter that is smaller than the diameter of the plunger.

Advantageously, the plunger has an axial length that is 50% to 300% of the diameter of the plunger. Preferably, the axial length is greater than the diameter.

The inventive syringe, due to the use of sintered material having substantially uniform pores between the sintered particles, provides for automatic venting of the syringe upon placing of the plunger into the open end of the cylinder, even when air bubbles are enclosed without the need for polymerization of the dental material at the end facing the plunger.

Surprisingly, it has been found that no dental material can pass through the plunger, This is achieved by selecting the size of the pores such that the surface tension of the dental material prevents passage through the pores.

However, a satisfactory sealing action between the porous plunger and the cylinder wall results whereby the presence of the sintered plastic material is of special importance. Sintered polyethylene deforms when pressure is applied onto the end face of the plunger so that a depression results. By compression of the material the pores within the sintered material are made smaller and, on the other hand, a lateral pressure is exerted which provides a sealing action relative to the cylinder wall.

Surprisingly, no further measures such as providing a sealing ring etc. are required whereby it is understood that, depending on the application situation, it is possible to provide between the plunger and the push rod a small sealing ring.

Surprisingly, the desired effects of venting, on the one hand, and sealing, on the other hand, are already achievable for a pore size of 70 micrometer, but also for micropores of 5 micrometer. The inventive plungers made of sintered polyethylene are also stable for extended storage when the dental material comprising monomers is in contact for weeks with the plunger, although the hydrophobic properties of the plunger cause a certain softening or swelling of the plunger at the side facing the dental material.

Experiments carried out with the inventive syringe have shown that a strong deformation of the plunger, even for great dispensing pressures, do not occur, while, on the other hand, the slight deformation of the surface facing the push rod is desirable in order to achieve material compression.

The manufacture of the inventive plunger can be performed in any suitable manner. For example, the plunger can be stamped from a plate of sintered polyethylene whereby the thickness of the polyethylene plate defines the length of the plunger. Preferably, this length is somewhat greater than the diameter of the plunger so that a comparatively high air absorption and buffer capacity of the plunger is provided.

It is understood that the pore size of the plunger must be adapted to the surface tension of the material to be dispensed. In this context it is important to provide a hydrophobic embodiment of the sintered material because a capillary action must be avoided especially for long term storage.

BRIEF DESCRIPTION OF THE DRAWINGS

The object and advantages of the present invention will appear more clearly from the following specification in conjunction with the accompanying only drawing, in which the inventive syringe is shown partially in section whereby a push rod pushes on the end of the plunger opposite the dispensing socket.

DESCRIPTION OF PREFERRED EMBODIMENTS

The present invention will now be described in detail with the aid of a specific embodiment utilizing the only Figure.

The inventive syringe 10 has a cylinder 12 in which the inventive piston 14 is slidably supported. The cylinder 12 is open at the right end 16 and has at the opposite end a dispensing socket 17 for example, embodied as suggested in U.S. Pat. No. 5,938,439 the disclosure of which is incorporated by reference into the present application.

It is understood that any suitable other embodiment of the dispensing socket is possible.

The syringe 10 is filled with dental material 18 which must be dispensed through the dispensing socket. For applying the dispensing force, a push rod 20 is provided that exerts a pressure force onto the plunger 14.

The plunger 14 is comprised of sintered polyethylene with a pore width of 70 micrometer which corresponds to a filter mesh site of 5 micrometer. The dental material 18 is present in a liquid, slightly viscous form. The plunger 14 is porous whereby the surface tension of the dental material 18, however, is sufficient in order to prevent the dental material from penetrating the micropores of the plunger 14.

When placing the plunger 14 onto the dental material 18, air may be enclosed but can penetrate into the micropores and can be passed through the plunger 14 via the micropores. When placing the plunger into the cylinder, only a slight pressure must be applied since the air can pass through the plunger 14 and the dental material 18 is not yet pressed out. Accordingly, the plunger 14 in this state is not yet deformed.

The figure shows the deformation of the plunger 14 during dispensing by the push rod 20. The push rod 20 has at its leading end 22 a bevel or rounded portion 24 which reduces the risk for notching. The compression deforms the plunger in the contact area with the push rod 20 such that its surface 26 facing the push rod 20 is centrally compressed.

Since the diameter of the push rod 20 is somewhat smaller than the diameter of the plunger 12, the compression does not take place over the entire surface area of the surface 26 but only at the center. Due to the rounded embodiment a slightly diverging force introduction takes place, as indicated by arrows 30 in the Figure, at the transition of the center area and the outer area 28 of the surface 26. This force introduction results in a compression of the sintered material of the plunger 14 and also in an increased pressure between the inner wall of the cylinder 12 and the plunger 14 at its rearward end. This measure results in an additional sealing action so that, when a corresponding pressure is applied onto the push rod 20, the dental material 18 cannot be squeezed past the plunger 14.

The greater the applied pressure, the greater the tendency of the dental material 18 to be forced into the pores of the plunger 14, but, at the same time, the compression of the piston relative to the wall of the cylinder 12 provides for an added sealing action. This self-reinforcing effect of the sealing action is inventively especially advantageous whereby it is understood that the precise design of the leading surface of the push rod can be adapted within a wide range to specific requirements and especially to the stability properties of the plunger 14.

The present invention is, of course, in no way restricted to the specific disclosure of the specification and drawings, but also encompasses any modifications within the scope of the appended claims.

What is claimed is:

1. A syringe for dispensing dental material, said syringe comprising:

a cylinder having a dispensing socket and an open end opposite said dispensing socket; and a plunger inserted through said open end into said cylinder and guided in said cylinder, said plunger being formed entirely of porous, sintered pressure deformable polyethylene.

2. A syringe according to claim 1, wherein said porous, sintered polyethylene has pores of a pore diameter of 2 to 8 micrometer measured according to DIN 30911 and/or ISO 4003.

3. A syringe according to claim 2, wherein said pore diameter is 5 micrometer.

4. A Syringe according to claim 1, wherein said pore size of said porous, sintered polyethylene is 50 to 120 micrometer measured according to DIN 30911 and/or ISO 4003.

5. A syringe according to claim 4, wherein said pore size is 70 micrometer.

6. A syringe according to claim 1, wherein said porous, sintered polyethylene has a porosity of 30 to 60%.

7. A syringe according to claim 1, wherein said porous, sintered polyethylene has micropores.

8. A syringe according to claim 1, wherein said polyethylene contains a binder for increasing stability.

9. A syringe according to claim 1, wherein said porous, sintered polyethylene has a density of 0.4 to 0.8 g/cm$^3$.

10. A syringe according to claim 1, wherein said porous, sintered polyethylene has a density of 0.6 g/cm$^3$.

11. A syringe according to claim 1, further comprising a push rod acting on an end of said plunger facing away from said dispensing socket for elastically deforming said plunger, wherein said push rod has a diameter that is smaller than a diameter of said plunger.

12. A syringe according to claim 11 wherein said push rod has a beveled or rounded end.

13. A syringe according to claim 12 wherein said plunger has a recessed portion which is engaged by the beveled or rounded portion of the push rod so that the plunger is deformed towards the walls of the cylinder to provide an additional sealing area.

14. A syringe according to claim 1, wherein said plunger has an axial length that is 50 to 300% of a diameter of said plunger.

15. A syringe according to claim 14, wherein said axial length is greater than said diameter.

* * * * *